United States Patent [19]

Kocache et al.

[11] Patent Number: 5,549,871
[45] Date of Patent: Aug. 27, 1996

[54] SENSOR FOR COMBUSTIBLE GASES

[75] Inventors: Riad M. A. Kocache; Dany F. Holman, both of Crowborough; James Swan, Eastbourne, all of United Kingdom

[73] Assignee: Servomex PLC, East Sussex, England

[21] Appl. No.: 542,713

[22] Filed: Oct. 13, 1995

Related U.S. Application Data

[63] Continuation of Ser. No. 416,449, Apr. 3, 1995, abandoned, which is a continuation of Ser. No. 185,741, Jan. 21, 1994, abandoned.

[30] Foreign Application Priority Data

Jan. 21, 1993 [GB] United Kingdom ............... 9301104

[51] Int. Cl.$^6$ .................................................. G01N 27/16
[52] U.S. Cl. ........................................ 422/95; 338/34
[58] Field of Search ........................ 422/94–98; 338/25, 338/34

[56] References Cited

U.S. PATENT DOCUMENTS

| | | | |
|---|---|---|---|
| 3,092,799 | 6/1963 | Baker | 338/34 |
| 3,200,011 | 8/1965 | Baker | 126/181 |
| 3,564,474 | 2/1971 | Firth et al. | 338/25 |
| 4,325,912 | 4/1982 | Sawa et al. | 422/95 |
| 4,355,056 | 10/1982 | Dalla Betta et al. | 422/94 X |
| 4,572,900 | 2/1986 | Wohltjen | 422/94 X |
| 4,870,025 | 9/1989 | Hurley et al. | 422/95 X |
| 5,338,515 | 8/1994 | Dalla Betta et al. | 422/95 |

FOREIGN PATENT DOCUMENTS

| | | | |
|---|---|---|---|
| 5316309 | 5/1978 | Japan | 422/95 |

*Primary Examiner*—Jeffrey Snay
*Attorney, Agent, or Firm*—Cumpston & Shaw

[57] ABSTRACT

A combustible gas sensor comprises four glass insulated radially extended and symmetrical temperature sensitive elements which are coated with a porous ceramic but only two elements having a catalyst. The sensor is mounted inside a temperature controlled reactor vessel in a region of no temperature gradient into which a combustible gas mixture is admitted and reacted on the catalytic surfaces. The change in the resistance of the elements under the catalyst is a measure of the concentration of the combustible gas.

35 Claims, 5 Drawing Sheets

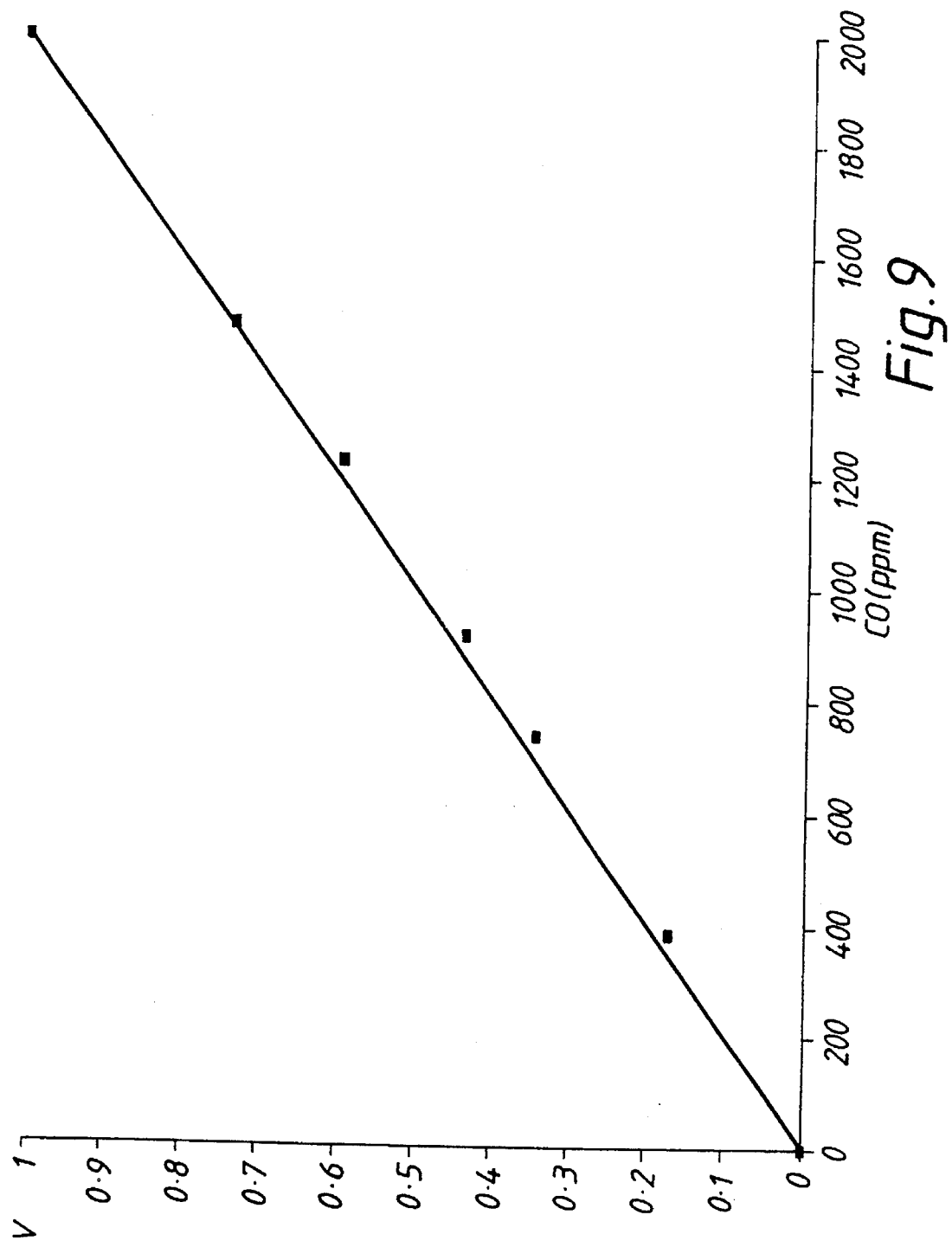

SENSOR FOR COMBUSTIBLE GASES

This application is a continuation of application Ser. No. 08/416,449, filed on Apr. 3, 1995, now abandoned, which is a continuation of Ser. No. 08/185,741, filed on Jan. 21, 1994, now abandoned.

FIELD OF THE INVENTION

The present invention relates to a sensor, of the catalytic calorimeter type, for sensing the concentration of combustible gases in a gas mixture.

BACKGROUND OF THE INVENTION

Combustible gases in the presence of oxygen create a hazardous mixture; mines, tankers and many industrial processes are exposed to or handle such mixtures. Industrial safety requires the monitoring and control of such mixtures in such environments. The energy industry on the other hand combusts such mixtures under control to create energy and is also interested in the monitoring and control of such mixtures for optimising efficiency.

Devices based on the monitoring of the change in the resistance of a temperature dependent and catalytic element and relating this change to the concentration of a combustible gas which is catalytically combusted on the element, have been available for many years. The simplest is just a heated platinum wire forming a part of a wheatstone bridge. The 'Pellistor' is probably the most common form of this type of device (U.S. Pat. Nos. 3,092,799/63, 3,200,011/65, 3,564,474/71). In its basic form it consists of a platinum coil which acts both as a heater and as a temperature sensor. The coil is encapsulated by a refractory pellet of porous alumina in which a catalyst is dispersed in one element. The platinum coil heats the catalyst to a suitable temperature at which the oxidation of the combustible gas is induced on the surface of the catalyst. The heat generated will be conducted to the coil and raise its temperature and hence alter its resistance. A coil in a pellet with no catalyst is used as a reference.

SUMMARY OF THE INVENTION

The present invention has as an object the provision of a catalytic calorimeter for sensing combustible gases which has increased sensitivity as compared to the known devices mentioned above.

The present invention provides a sensor for a combustible gas comprising:

a chamber, having inlet means and outlet means, the chamber being adapted to direct a gas to be tested along a flow path through said chamber from said inlet means to said outlet means;

heater means arranged to heat the chamber and its contents to a predetermined temperature; and an even number of substantially identical temperature sensitive resistive elements arranged within the chamber and symmetrically with respect to said flow path, half of said elements being sensing elements and having a catalyst associated therewith to facilitate combustion of said combustible gas in the vicinity of said sensing elements thereby increasing their temperature, the remainder of said elements being reference elements not having a catalyst associated therewith.

Important features of the present invention include the separation of the functions of heating the gas to reaction temperature and sensing the combustion with temperature sensitive elements. This enables the temperature sensitive elements to be specifically designed to optimise this function. In the present invention there are provided reference temperature sensitive elements which do not have catalyst associated with them. The reference elements and the sensing elements are arranged to be accurately symmetrical with the regard to the gas flow so as to provide the best possible cancellation of effects not associated with the combusting of the combustible gas.

The above mentioned separation also means that the heater for the chamber can be independently designed to provide proper heating of the chamber sensors and gas. To increase the sensitivity it is preferable to ensure that the sensor is heated to be at the required reaction temperature and the gas is also at that temperature as it reaches the sensor. In the preferred embodiment the sensor is positioned within a heated vessel at a location of very small or zero temperature gradient.

Preferably the invention comprises four identical temperature sensitive elements fabricated on a ceramic substrate symmetrically arranged around a central point. Alternate ones of the elements are associated with a catalyst which then become the sensing elements and the others are reference elements. The catalyst is preferably disposed in a porous substrate covering the elements. The change in the value of the resistance of the elements under the reactive elements due to the catalytic oxidation of the combustible gas on the surface of the catalyst raising the local temperature, is used to monitor the concentration of the combustible gas.

The invention will be better understood from the following description of a preferred embodiment, given by way of example and with respect to the attached drawings, in which:

BRIEF DESCRIPTION OF THE DRAWINGS

FIG. 9 is a graph illustrating typical experimental results achieved with a device made according to the preferred embodiment of the invention.

DETAILED DESCRIPTION OF THE INVENTION

In the preferred embodiment of this invention, four temperature sensitive and radially extended elements are formed symmetrically on a thin substrate by a suitable process such as thick or thin film technology. The temperature sensitive element could be a material such as platinum, a semiconductor (thermistor) suitably manufactured or a material such as diamond powder thin film thermistor suitably deposited which displays temperature dependent behaviour.

Figure 1:
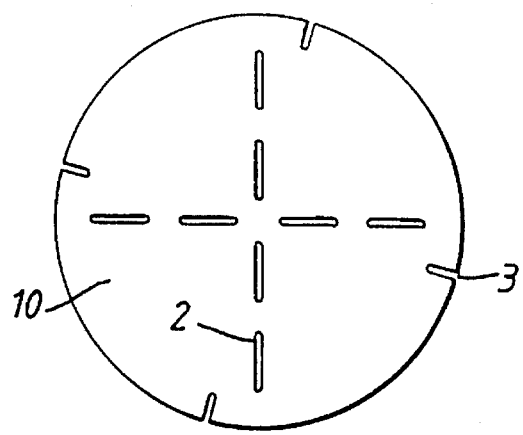
FIG. 1 illustrates the form of a substrate used in the preferred embodiment.
Figure 2A:
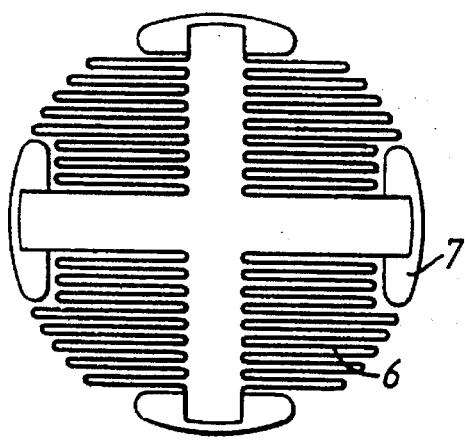
FIGS. 2(a) and 2(b) show two possible configurations of the sensor elements in the preferred embodiment.

The substrate 10, shown in FIG. 1, is made of a material with poor heat conductivity properties such as a suitable ceramic, and has to be thin so that it can be positioned inside the reactor under a region of constant temperature where it will suffer no temperature gradients. In addition the use of a thin section reduces heat exchange to the surroundings and between the separate elements. This heat exchange between elements is further reduced by the choice of substrate material and by the inclusion of thin slots 2 between elements so as to break the heat conductive paths. The slots 2 also allow the gas from under the element to move to the top of the element encouraging proper gas exchange. As only two of the elements have a catalyst dispersed above them and the other two act as reference elements with no combustion over them, it is very important that no heat from the catalytic elements finds its way to the reference elements, as this would reduce the sensitivity. The four sensor elements have to be as near identical as possible. FIGS. 2(a) and (b) show two suitable designs as examples, comprising the track of the resistive elements 6 and pads 7 to which the lead wires are connected. What is important is that the elements are as near identical as possible in their electrical characteristics (resistance value and sensitivity to temperature) and in their physical form, so as to reduce the common mode effects such as those due to the thermal conductivity of the background non combusting gases, the effect of flow variation, changes in the ambient temperature and in the temperature of the sample gas and so on.

The four elements are covered with a very thin glass layer which electrically insulates them from any overlays; but is thin enough to allow the heat to conduct to the elements. Each of the four elements is then covered with a uniform porous ceramic coating; but only in the ceramic above two diametrically opposed elements is the catalyst dispersed. Alternatively two diametrically opposed elements can be sealed with glass or any other inert coating whilst the other two treated as described earlier and doped with a catalyst. The catalyst could be one of the precious metals or their oxides (Pt, Rh, Ir, Pd . . . ) or any other suitable catalyst chosen usually to suit the combustible gas required to be monitored. It could be applied mixed with the ceramic, or dispersed as a compound which is decomposed later, or electro-deposited. It is important to disperse only the appropriate amount of catalyst. Too little will lead to loss of sensitivity, and too much leads to eventual sintering and blocking of pores in the ceramic.

Figure 3:
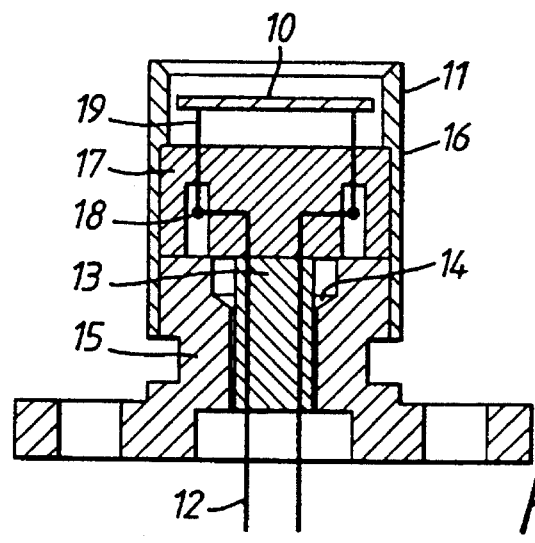
FIG. 3 is a sectional view of the sensor head unit of the preferred embodiment.

As shown in FIG. 3 substrate 10 is mounted inside a protective shroud assembly 11 which is seated by way of ledge 16, on a ceramic table 17 and fits onto the end assembly 15. The table 17 sits on the end assembly 15 and centrally over a four bore ceramic unit 13. Wires 12 to the four element sensor are hermetically sealed within the four bore ceramic unit 13 which is itself hermetically sealed at surface 14 to the metallic end assembly 15.

Figure 4:
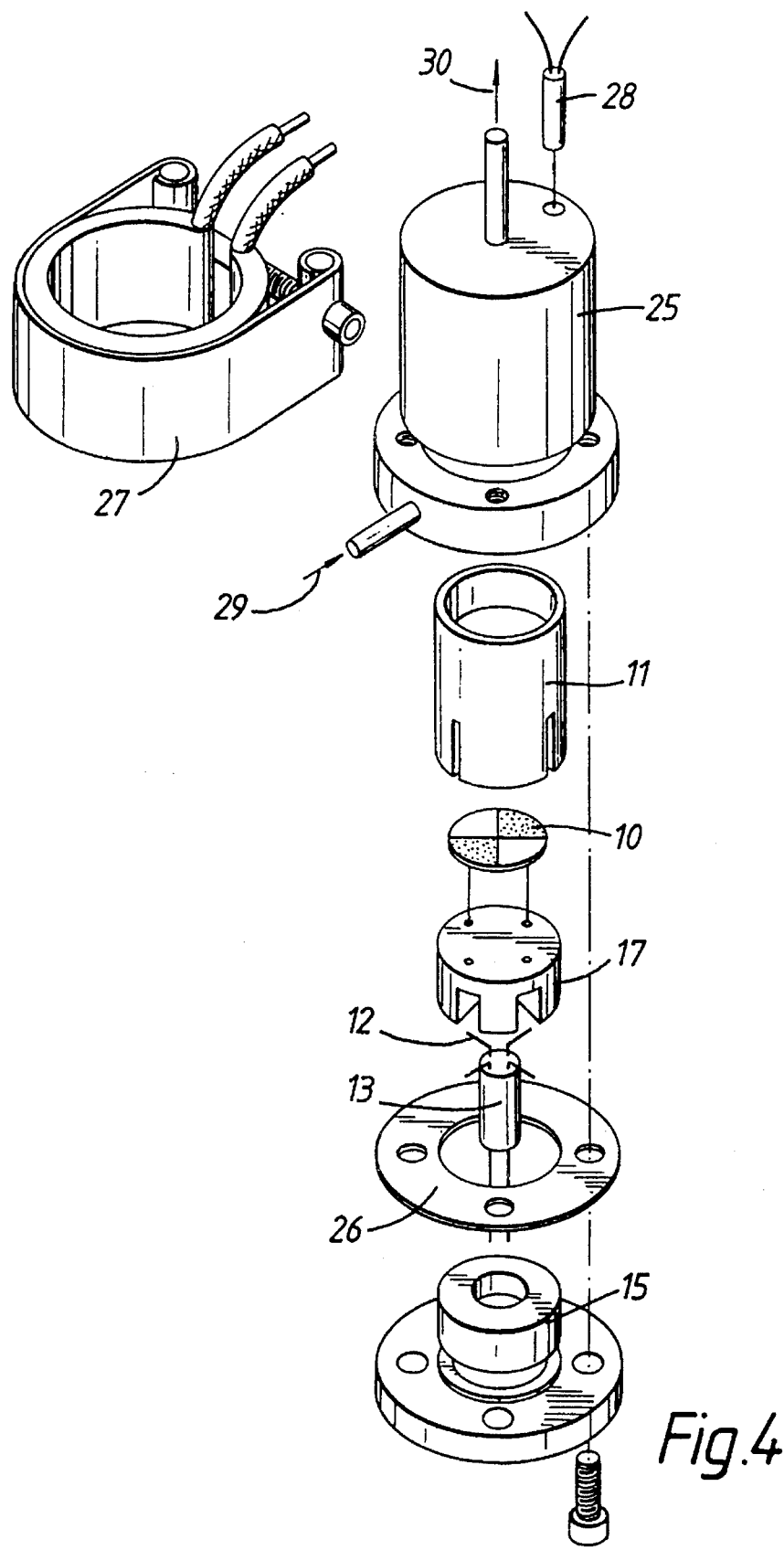
FIG. 4 is an exploded view of the sensor device according to the preferred embodiment.

The total assembly of the sensor device, including the parts shown in FIG. 3 is shown in FIG. 4. The sensor head unit is inserted into a suitably designed reactor vessel 25 and screwed gas tight through an appropriate seal 26 at the end. The reactor vessel is spatially heated on the outside by an appropriate heater 27 that surrounds tightly the reactor vessel. With the aid of a temperature sensor, such as a platinum resistance thermometer 28, and appropriate electronics the temperature inside the reactor is controlled.

Figure 5:
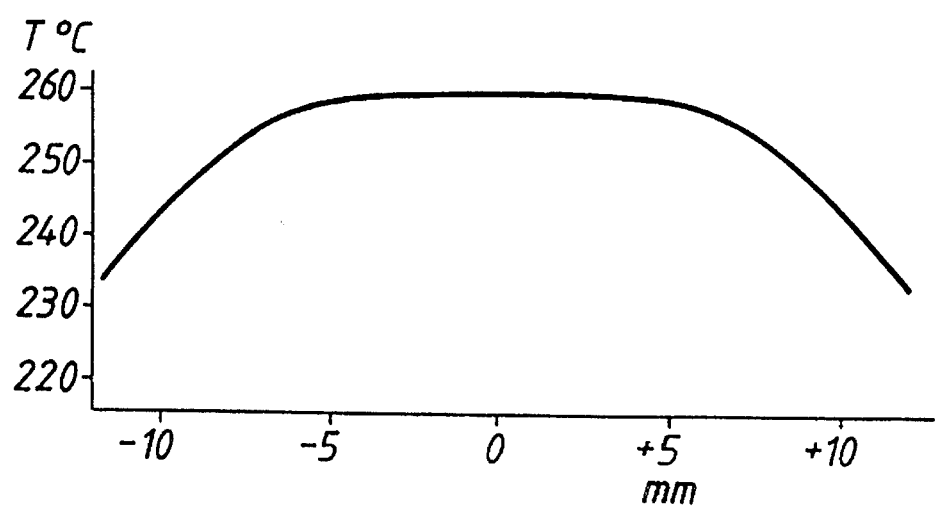
FIG. 5 illustrates the temperature distribution within the reactor vessel of FIG. 4.

The temperature sensor position within the body is chosen carefully so that the sensor position is in the flat portion of the temperature profile along the axis of the reactor as shown in FIG. 5, which shows temperature plotted against distance from the sensor plate. As is apparent, the temperature distribution inside the reactor peaks and flattens at a position nearly in the middle of the reactor across its longitudinal axis and tails off nearly symmetrically towards each end. (The plot of FIG. 5 was obtained for a reaction temperature of 260° C., with the external ambient temperature being 25° C.)

The sensor element 10 is positioned with its plane perpendicular to the axis of the reactor and at a point where the temperature gradient is nearly flat. This positioning and the fact that the element is very thin ensures very constant ambient temperature conditions around the sensor, and hence allows the sensor to resolve the very small temperature changes on its catalytic surface.

Figure 6:
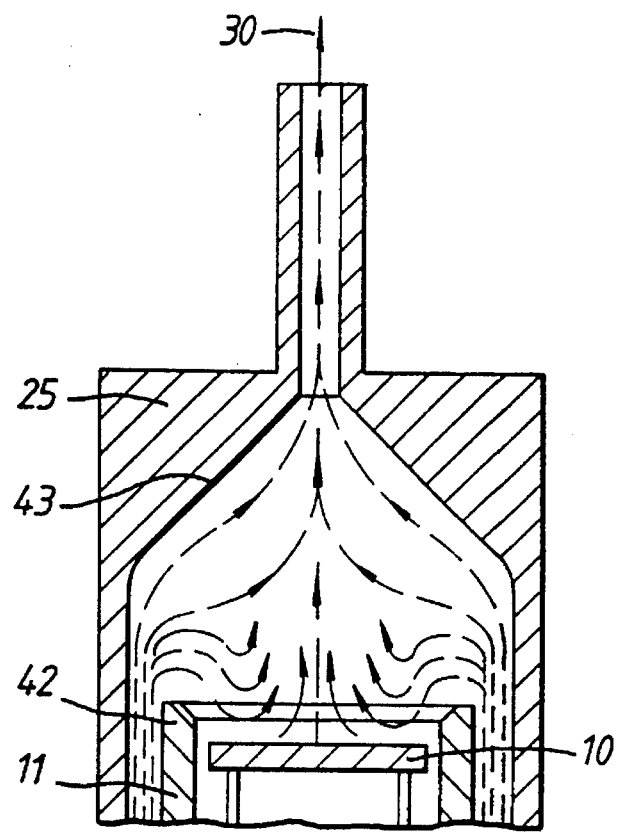
FIG. 6 is a sectional view of the reactor vessel illustrating the gas flow within the vessel.

The gas mixture is admitted to one end of the reactor indicated by arrow 29 and distributed round the inside of the body of the reactor, and the outside shroud of the element, so that it gradually reaches the inner temperature of the reactor, and at the point of low temperature gradient the gas has attained exactly the temperature of that region. The incoming gas, at that point, is induced to turn in partially towards the element as shown in FIG. 6 by the shaping 42 of the inner side of the shroud and the top inner end 43 of the vessel 25. A combination of flow and diffusion causes the gas to reach the surface of the element where the catalytic reaction takes place. The products of combustion 40 join some of the incoming gas and leave the vessel through outlet pipe 30. This is encouraged by the shape of the top part of the inner side of the reactor vessel 43.

In the above it is very important that the incoming gas should reach the same temperature of the elements and that the sensor disc should be positioned at the flat part of the temperature gradient inside the vessel. It is also important that the inside and particularly the top part of the reactor vessel is designed so that the element is not exposed to direct fast gas flow. The element should receive only very low direct flow and the arrival of gas at this sensor element should be mainly due to diffusion. The main part of the gas flow induces the gases at the surface of the element to be sucked to the outlet thereby removing the products of combustion and enabling fresh gas to arrive at the surface of the element.

The four element sensor can be connected as a bridge circuit (DC or AC) with the non catalytic elements acting as reference units and the catalysed elements as combustible gas sensitive units. The bridge is balanced in the presence of a non-combustible gas such as air, and calibrated by admitting a combustible/air gas mixture of known concentration. With appropriate electronic circuitry and display the unbalance in the bridge due to the catalytic combustion of the combustible gas altering the resistance of the elements underneath it due to the resultant heat generated may be related to the concentration of the combustible gas. The choice of gas necessitates a choice of appropriate catalyst and appropriate operating temperature.

In the following, particularly preferred materials and dimensions for the components of the arrangement described above are described.

A thin (0.2 mm) stabilized zirconia disc (10 mm diameter) is chosen for the substrate. The zirconia has about four times worse thermal conductivity than alumina thus minimizing the heat feedback from the catalytic elements, which are heated by the combustion, to the non catalytic elements (reference elements). Fused quartz is another possible material for a substrate and the choice should be part of an overall material compatibility view. Slots 2 shown in FIG. 1 in a cross formation divide the disc into four quadrants. The shape of the slots and their dimensions (about 0.15×1.5 mm) aim to increase the thermal resistance between the quadrants and hence reduce thermal feedback between elements without compromising the strength of the disc. The slots also provide a path for the gases under the disc to find their way to the surface of the disc thus improving gas circulation. The disc has also four notches 3 on its outer perimeter (0.15×0.7 mm). These provide anchor points for the lead wires and take the strain off the weld points. They are equally spaced around the perimeter of the disc and slightly displaced to one side of the cross pattern. This ensures their correct positioning in respect to the termination of the resistive elements.

Figure 2B:
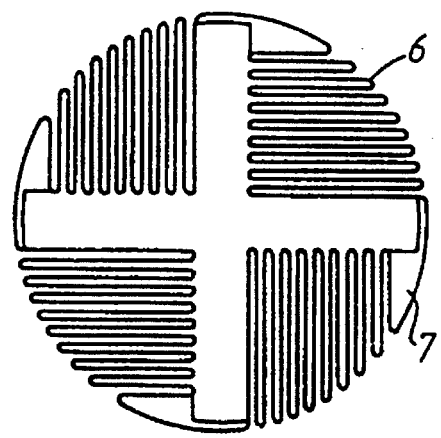

Four identical resistive elements are produced one on each quadrant. The designs shown in FIGS. 2(*a*) & 2(*b*) are for thick film screen printing technology, although other technologies of producing the elements may be used. The design of the pattern should be considered in conjunction with the technology to be used to implemented it and should aim to produce as nearly as possible identical electrical and spatial characteristics. Each of patterns a or b produce the right characteristics if used with the right screens. A platinum resistor ink such as Engelhardt T-11502 produces very good elements when fired and sintered correctly, these can be further matched so that the resistor bridge elements are matched to better than 0.1%.

One side of the end termination 7 of each resistor 6 overlaps the notches 3 described earlier so that a platinum/10% Ir wire of about 0.2 mm diameter, which is slightly flattened on its end can be brought through the notch, bent over the pad and soldered, welded or cemented to it with Pt paste; ensuring thus a good ohmic contact. The symmetry of the design and the positioning of the disc under a constant temperature ensures that the thermoelectric effects are negligible. This wire is preferred because its thermal coefficient of expansion is near that of the zirconia and because the alloy is stronger than pure platinum wire.

A very thin electrically insulating glass coating is then applied over all the disc uniformly covering all four elements. A glass such as Hereaus Cermallay-EMD1-9053 would provide suitable cover.

A slurry of zirconia is then screened over the elements and fired appropriately to provide a stable and porous matrix of about 0.1 mm thick and of an average pore size of about 0.5–5 microns. Other suitable ceramic materials could be used, such as alumina for example.

The chosen catalyst, platinum in the case of sensing CO as the combustible gas, may be premixed as a very fine powder in the zirconia slurry. A simpler way of introducing it is to use chloroplatinic acid, dispersed on the two required elements and then heated to decomposition to form platinum. Other techniques such as electroplating may be used.

A final thin coat of ceramic (e.g zirconia, alumina) may be added if extra protection is needed to the surface. It acts effectively as a filter. Its presence usually reduces the sensitivity of the sensor. Again the non-catalytic reference elements can be sealed by material other than zirconia e.g. glass.

Figure 7A:
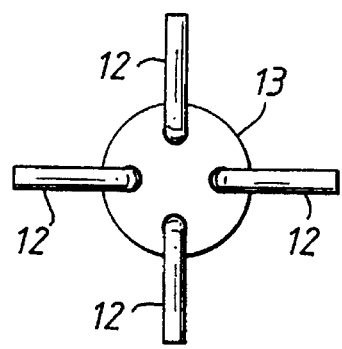
FIGS. 7(a)–7(b) and 8(a)–8(c) illustrate the specific preferred construction of some parts of the sensor according to the preferred embodiment.
Figure 7B:
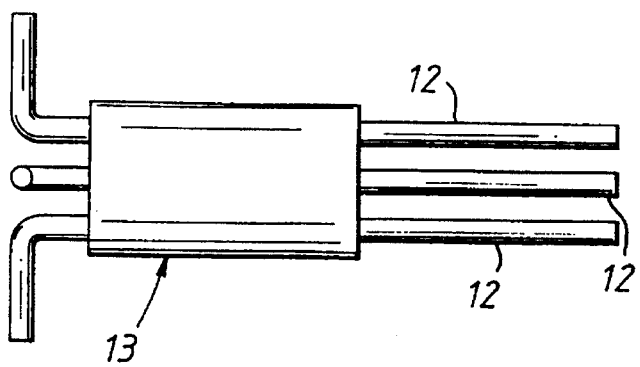
Figure 8A:
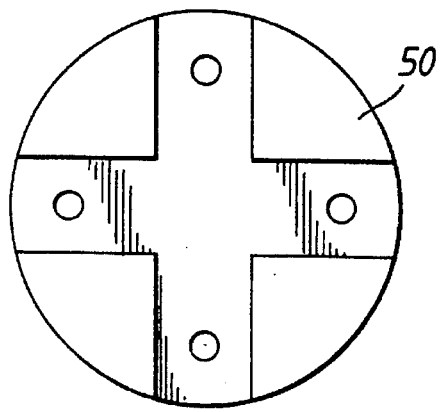
Figure 8B:
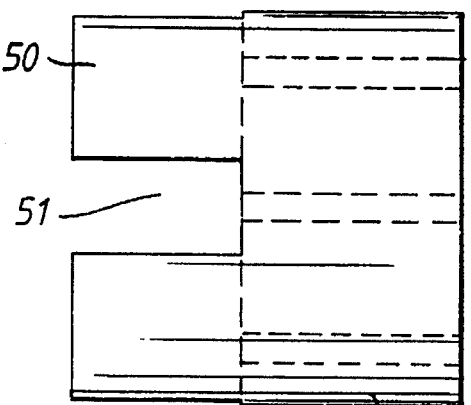
Figure 8C:
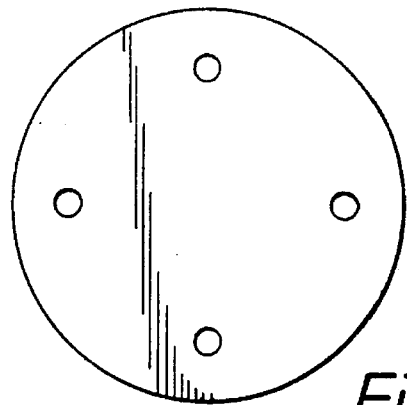

A short length of four bore alumina rod 13 (about 6 mm long, 5 mm diameter and 0.75 bore) shown in end and side views in FIGS. 7(*a*) and 7(*b*) has four lengths of nicrome wire 12 hermetically sealed into it with appropriate sealing glass and at the same time the rod is sealed into the stainless steel base 15 with the same glass 14. Table 17 shown in first and second ends and side views in FIGS. 8(*a*), 8(*b*) and 8(*c*) (14 mm diameter 2 mm top and 6 mm legs) has four holes in the top (c) which the wires from the disc go through leaving the disc about 1 mm above the table. The lower end of the table is cut across like a cross (a) leaving effectively four legs 50 for positioning and seating correctly on the rod and inside the shroud, and allowing space 51 to house the wires and access to weld them or fuse them from the side. The wires from the disc and those from the rod are bent and welded together. The slots under the table leave ample space to do that. A stainless steel shroud 11 is pushed into position aligning the table with the base until its inner edge 16 rests on the top of the table. Suitable lead wires are connected to the end wires.

The sensor head is then pushed into the reactor unit 25 which is made of stainless steel, and sealed gas tight with screws and a high temperature gasket 26. The temperature sensor 28 and the heater 27 are placed in the correct places.

The temperature control system (not shown) which drives the heater 27 and senses the temperature by the platinum resistance thermometer 28 ensures constant operating temperature. For CO a good operating temperature is 280 degrees Centigrade. An oscillator feeds the bridge with AC and the output is initially balanced when air is passed through the reactor. The electronic system is calibrated to read zero. A span gas say 2000 ppm CO in air is admitted into the reactor, the balance of the bridge is disturbed and a voltage output from the electronic system say 1 volt will correspond to 2000 ppm CO. FIG. 9, which is a plot of output voltage against CO(ppm), shows a typical curve of voltage output against the gas concentration.

The advantages of the system described become apparent on examining the results. The high sensitivity allows the resolution of about a few ppm CO; an improvement of at least 10 times of what was possible earlier with devices such as Pellistors. The effect of water vapour and ambient gases are reduced by a factor of at least ten, improving the baseline stability and permitting lower ranges to be monitored.

We claim:
1. A sensor for a combustible gas comprising:
   a temperature sensitive element having a catalyst associated therewith to facilitate combustion of the combustible gas;
   a shroud surrounding the temperature sensitive element and extending above a top surface of the temperature sensitive element;
   a reaction vessel surrounding the shroud and forming a passageway there between for creating a flow of gas separated from the temperature sensitive element by the shroud and having a shaped downstream end for directing the flow inwardly starting at a point above the temperature sensitive element so that the flow of gas does not directly contact the temperature sensitive element, but reaches the temperature sensitive element substantially solely by diffusion; and
   a heater coupled to the reaction vessel.
2. The sensor according to claim 1, further comprising a temperature sensor extending through a hole in the shaped end of the vessel for ensuring that gas flowing over the temperature sensitive element is heated to a predetermined temperature.
3. The sensor according to claim 1, in which the reaction vessel further comprises a gas outlet at the shaped downstream end and a gas inlet at an opposite upstream end.
4. The sensor according to claim 3, in which the shroud comprises a cylinder having a diameter larger than the temperature sensitive element.
5. The sensor according to claim 4, in which the reaction vessel comprises a cylindrical portion having an inside diameter larger than an outside diameter of the shroud for forming an annular passageway there between.

6. The sensor according to claim 5, in which the inlet comprises a port in the reaction vessel communicating with the annular passageway.

7. The sensor according to claim 6, having a closed end sealed to the shroud and the reaction vessel, and the shroud has an opposite open end.

8. The sensor according to claim 3, wherein the arrangement of the heater, the reaction vessel and the shroud provides a region with a substantially zero temperature gradient within the vessel and in which region the temperature sensitive element is positioned.

9. The sensor according to claim 8, in which the temperature sensitive element comprises a thin substrate, an even number of substantially identical temperature sensitive resistive elements arranged symmetrically on the substrate, half of the resistive elements being sensing elements and having said catalyst associated therewith to facilitate combustion of the combustible gas in the vicinity of the sensing elements thereby increasing their temperature, the remainder of the resistive elements being reference elements not having a catalyst associated therewith.

10. The sensor according to claim 9, in which the temperature sensitive resistive elements are positioned on a plane at the region of substantially zero temperature gradient within the vessel.

11. The sensor according to claim 9, comprising an inert coating on the reference elements and a catalytic doping on the sensing elements.

12. The sensor according to claim 9, in which the substrate further comprises slots between the resistive elements for reducing thermal feedback between the resistive elements.

13. The sensor according to claim 9, in which the temperature sensitive resistive element comprises platinum.

14. The sensor according to claim 9, in which there are four temperature sensitive resistive elements and the sensing elements are diametrically opposed to each other.

15. The sensor according to claim 9, in which the temperature sensitive resistive elements are formed by one of thick and thin film technology.

16. The sensor according to claim 9, in which the thin substrate is about 0.2 mm thick.

17. The sensor according to claim 9, in which the catalyst is selected from Pt, Rh, Ir and Pd.

18. The sensor according to claim 9, in which the substrate comprises a low thermal conductivity material selected from a ceramic and a glass.

19. The sensor according to claim 18, in which the ceramic comprises a stabilized zirconia.

20. The sensor according to claim 9, in which the temperature sensitive resistive elements are covered by an electrically insulating layer.

21. The sensor according to claim 20, in which the insulating layer is a glass layer.

22. The sensor according to claim 20, in which the insulating layer is covered by a first porous ceramic coating.

23. The sensor according to claim 22 in which the first porous ceramic coating is selected from a zirconia and an alumina.

24. The sensor according to claim 22, in which the catalyst is disposed in the first porous ceramic coating above the sensing elements.

25. The sensor according to claim 24, in which the temperature sensitive resistive elements are covered by a second porous ceramic coating.

26. A sensor for a combustible gas comprising:

a reaction vessel having a chamber therein, the vessel having an open base end, an intermediate cylindrical portion, a shaped opposite end, a gas inlet for directing the gas into the base end, and a gas outlet for exhausting the gas from the shaped end;

a heater coupled to the vessel;

a sensor head within the cylindrical portion of the vessel comprising; a metallic tubular end assembly having a base end and an opposite end; a cylindrical insulating unit hermetically sealed within the tubular end assembly; a plurality of conducting wires, each one of the wires hermetically sealed in the insulating unit and passing there through; a ceramic table seated on the opposite end of the tubular end assembly and having a plurality of holes extending axially there through, a sensor plate positioned perpendicular to the axis of the sensor above the ceramic table and rigidly connected by a plurality of electrically conducting leads to the plurality of conducting wires via the holes; the sensor plate comprising a thin substrate, an even number of substantially identical temperature sensitive resistive elements arranged symmetrically on the substrate, half of the elements being sensing elements and having a catalyst associated therewith to facilitate combustion of the combustible gas in the vicinity of the sensing elements thereby increasing their temperature, the remainder of the elements being reference elements not having a catalyst associated therewith; and a cylindrical shroud surrounding the sensor head and extending from the base end of the tubular assembly to between the sensor plate and the shaped end and forming an annular passageway between the reaction vessel and the shroud for creating a flow of gas separated from the sensor plate by the shroud and directing the flow inwardly starting at a point beyond the sensor plate so that the flow of gas does not directly contact the sensor plate, but reaches the sensor plate substantially solely by diffusion, wherein the gas inlet communicates with the annular passageway.

27. The sensor according to claim 26, in which the catalyst is selected from Pt, Rh, Ir and Pd.

28. The sensor according to claim 26, in which the temperature sensitive resistive element comprises platinum.

29. The sensor according to claim 26, in which the cylindrical insulating unit is a ceramic unit.

30. The sensor according to claim 26, wherein the arrangement of the heater, the reaction vessel and the shroud provides a region with a substantially zero temperature gradient within the chamber and in which region the sensor plate is positioned.

31. The sensor according to claim 30, in which the temperature sensitive elements are positioned on a plane at the region of substantially zero temperature gradient within the chamber.

32. The sensor according to claim 26, further comprising a first mounting flange extending radially from the base end of the reaction vessel and a second mounting flange extending radially from the base end of the tubular end assembly and outside the vessel.

33. The sensor according to claim 32, further comprising a gasket between the first and second flanges.

34. The sensor according to claim 33, further comprising a gas seal between a top surface of the ceramic table and the protective shroud.

35. The sensor according to claim 34, in which the seal is a ceramic adhesive.

* * * * *